(12) United States Patent
Sabb et al.

(10) Patent No.: US 6,503,900 B2
(45) Date of Patent: Jan. 7, 2003

(54) [1,4]DIAZEPINO [6,7,1-JK ]CARBAZOLES AND DERIVATIVES

(75) Inventors: Annmarie Louise Sabb, Pennington, NJ (US); Gregory Scott Welmaker, Jackson, NJ (US); Robert Lewis Vogel, Stratford, NJ (US); Joan Eileen Sabalski, Yardville, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/017,738

(22) Filed: Nov. 2, 2001

(65) Prior Publication Data

US 2002/0086860 A1 Jul. 4, 2002

Related U.S. Application Data

(60) Provisional application No. 60/245,599, filed on Nov. 3, 2000.

(51) Int. Cl.$^7$ .................. A61K 31/55; C07D 243/00; A61P 25/00; A61P 25/24
(52) U.S. Cl. ....................... 514/219; 540/556
(58) Field of Search ................ 514/219; 540/556

(56) References Cited

U.S. PATENT DOCUMENTS 3,914,250 A * 10/1975 Kim .......................... 260/315

OTHER PUBLICATIONS

CAPLUS printout for Haerter et al., Schmidt Reaction of Tetrahydroquinolone Derivatives, Chimia, vol. 30, No. 2, pp. 50–52, 1976.*
Gregory E. Martin et al., J. Med. Chem., 1989, 1052–1056, 32.
J.L. Browning et al., Society for Neuroscience Abstracts, Oct. 1999, 2075, 25(2), Abstract 830.12.
Jackson B. Hester et al., J. Med. Chem., 1970, 827–835, 13.
Dong H. Kim, J. Heterocycle. Chem., 1976, 1187–92, 13(6).
H.P. Haerter et al., Chimia, 30, 50–52, (1976).

* cited by examiner

*Primary Examiner*—Brenda Coleman
(74) *Attorney, Agent, or Firm*—Rebecca R. Barrett

(57) ABSTRACT

This invention provides [1,4]diazepino[6,7,1-jk]carbazole compounds of the formula:

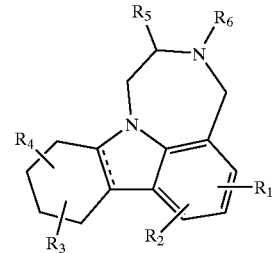

wherein: $R_1$ and $R_2$ are H, alkyl, alkoxy, halogen, fluorinated alkyl, —CN, —NH—SO$_2$-alkyl, —SO$_2$—NH-alkyl, alkyl amide, amino, alkylamino, dialkylamino, fluorinated alkoxy, acyl, phenoyl or thiophenoyl; $R_3$, $R_4$, $R_5$ and $R_6$ are H, alkyl, cycloalkyl, alkoxy or cycloalkoxy; $R_7$ is H or alkyl; $R_8$ is H or alkyl; and the dashed line indicates an optional double bond; or a pharmaceutically acceptable salt thereof, as well as methods and pharmaceutical compositions utilizing them for the treatment or prevention of disorders such as obsessive-compulsive disorder, depression, anxiety, schizophrenia, migraine, sleep disorders, eating disorders, obesity, epilepsy, and spinal cord injury.

16 Claims, No Drawings

[1,4]DIAZEPINO [6,7,1-JK ]CARBAZOLES AND DERIVATIVES

This application claims priority from copending provisional application Serial No. 60/245,599, filed Nov. 3, 2000, the entire disclosure of which is hereby incorporated by reference.

The present invention relates to new and known [1,4] diazepino[6,7,1-jk]carbazoles and derivatives thereof, which are serotonin 5-hydroxytryptamine $2_c$ ($5HT_{2C}$) receptor agonists useful for the treatment of disorders such as obsessive-compulsive disorder, depression, anxiety, generalized anxiety disorder, schizophrenia, panic disorder, migraine, sleep disorders, such as sleep apnea, eating disorders, such as hyperphagia, obesity, epilepsy, and spinal cord injury.

BACKGROUND OF THE INVENTION

Obesity is a medical disorder characterized by an excess of body fat or adipose tissue. Comorbidities associated with obesity are Type II diabetes, cardiovascular disease, hypertension, hyperlipidemia, stroke, osteoarthritis, sleep apnea, gall bladder disease, gout, some cancers, some infertility, and early mortality. As the percentage of obese individuals continues to rise both in the U.S. and abroad, obesity is expected to be a major health risk in the $21^{st}$ Century. The serotonin 5-hydroxytryptamine (5-HT) receptor is a G-protein coupled receptor which is expressed in neurons in many regions of the human central nervous system. [Wilkinson, L. O. and Dourish, C. T. in *Serotonin Receptor Subtypes: Basic and Clinical Aspects* (ed. Peroutka, S. J.) 147–210 (Wiley-Liss, N.Y., 1991).] The $5HT_{1C}$ receptor (formerly called the $5HT_{2C}$ receptor) is a prominent subtype of the serotonin receptor found in the central nervous system of both rats and humans. It is expressed widely in both cortical and subcortical regions. [Julius, D. MacDermott, A. B., Axel, R. Jessell, T. M. *Science* 241:558–564 (1988).] Studies in several animal species and in humans have shown that the non-selective $5HT_{2C}$ receptor agonist, meta-chlorophenylpiperazine (MCPP) decreases food intake. [Cowen, P. J., Clifford, E. M., Williams, C., Walsh, A. E. S., Fairburn, C. G. *Nature* 376: 557 (1995).] Tecott, et a/ have demonstrated that transgenic mice lacking the $5HT_{2C}$ receptor eat more and are heavier than Wild Type mice. [Tecott, L. H., Sun, L. M., Akana, S. F., Strack, A. M., Lowenstein, D. H., Dallman, M. F., Julius, D. *Nature* 374: 542–546 (1995).] Compounds of this invention are $5HT_{2C}$ receptor subtype selective agonists which are selective over other monoamine receptors, causes a reduction in food intake and result in a reduction in weight gain. Other therapeutic indications for $5HT_{2C}$ agonists are obsessive compulsive disorder, depression, panic disorder, schizophrenia, sleep disorders, eating disorders, epilepsy, and spinal cord injury.

U.S. Pat. No. 3,914,250 (Oct. 21, 1975) describes 1,4-diazepino[6,5,4-jk]carbazoles as anticonvulsant agents. This invention relates to new and known 1,4-diazepino[6,5,4-jk] carbazoles and derivatives which bind to and activate $5HT_{2C}$ receptors in the CNS and are useful for the treatment of CNS disorders which can benefit from modulation of the $5HT_{2C}$ receptor.

DESCRIPTION OF THE INVENTION

This invention provides compounds of formula I having the structure:

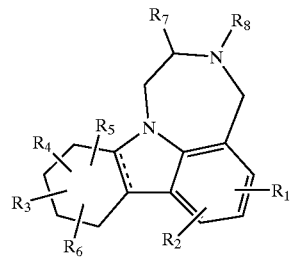

wherein:

$R_1$ and $R_2$ are independently selected from hydrogen, alkyl of 1–6 carbon atoms, alkoxy of 1–6 carbon atoms, halogen, fluorinated alkyl of 1–6 carbon atoms, —CN, —NH—SO$_2$-alkyl of 1–6 carbon atoms, —SO$_2$—NH-alkyl of 1–6 carbon atoms, alkyl amide of 1–6 carbon atoms, amino, alkylamino of 1–6 carbon atoms, dialkylamino of 1–6 carbon atoms per alkyl moiety, fluorinated alkoxy of 1–6 carbon atoms, acyl of 2–7 carbon atoms, phenoyl or thiophenoyl;

$R_3$, $R_4$, $R_5$ and $R_6$ are independently selected from hydrogen, $C_1$–$C_6$ alkyl, $C_3$–$C_6$ cycloalkyl, $C_1$–$C_6$ alkoxy or $C_3$–$C_6$ cycloalkoxy;

$R_7$ is hydrogen or $C_1$–$C_6$ alkyl;

$R_8$ is hydrogen or $C_1$–$C_6$ alkyl; and wherein the dashed line indicates an optional double bond;

or a pharmaceutically acceptable salt thereof.

In the definitions of $R_1$ and $R_2$ herein, the fluorinated alkyl and fluorinated alkoxy groups indicate the specified alkyl or alkoxy groups having any amount of fluorine substitution, including, but not limited to, groups such as —CHF$_2$, —CF$_3$, —C$_2$F$_5$, —OCF$_3$, etc.

A preferred group of compounds of this invention comprises those having the formula I, above, wherein $R_1$, $R_2$, $R_8$ and $R_7$ are each hydrogen and $R_3$, $R_4$, $R_5$ and $R_6$ are as defined above, or a pharmaceutically acceptable salt thereof. Another preferred group of compounds of this invention are those of Formula I wherein $R_1$, $R_2$, $R_5$, $R_6$, $R_8$ and $R_7$ are each hydrogen and $R_3$ and $R_4$ are as defined above, or a pharmaceutically acceptable salt thereof.

The $5HT_{2C}$ receptor agonists of this invention are useful for the treatment or prevention in mammals, preferably in humans, of disorders involving the central nervous system such as obsessive-compulsive disorder, depression, atypical depression, bipolar disorders, anxiety, generalized anxiety disorder, schizophrenia, psychoses, personality disorders, organic mental disorders, behavioral disorders associated with dementia or age-related conditions, aggressivity, drug and alcohol addiction, social phobias, sexual dysfunction, panic disorder, migraine, sleep disorders, such as sleep apnea, eating disorders, such as hyperphagia, bulimia or anorexia nervosa, obesity, epilepsy, and premenstrual tension.

This invention also includes methods of utilizing the compounds herein in treatments or preventitive regimens for treatment of central nervous system deficiencies associated with trauma, stroke, neurodegenerative diseases or toxic or infective CNS disorders including, but not limited to, encephalitis or menengitis; or cardiovascular disorders, including thrombosis; gastrointestinal disorders such as malfunction of gastrointestinal motility; and diabetes insipidus. These methods include the improvement or inhibition of further degradation of central nervous system activity during or following the malady or trauma in question. Included in these improvements are maintenance or improvement in motor and motility skills, control, coordination and strength. This invention includes methods for treating, preventing, modulating, ameliorating or improving the condition of each of these disorders in a mammal in need thereof, the methods comprising administering a therapeutically or pharmaceutically effective amount of a compound of this invention or a pharmaceutically acceptable salt thereof.

The compounds of this invention contain asymmetric carbon atoms and thus give rise to optical isomers and diastereoisomers. While shown without respect to stereochemistry in Formula I, the present invention includes such optical isomers and diastereoisomers; as well as the racemic and resolved, enantiomerically pure R and S stereoisomers, as well as other mixtures of the R and S stereoisomers and pharmaceutically acceptable salts thereof.

The term "alkyl" includes both straight- and branched-chain saturated aliphatic hydrocarbon groups and cycloalkyl groups. Halogen is defined as Cl, Br, F or I.

It will be understood that the dashed line in FIG. 1, above, indicates the optional reduction in the portion of the structure depicted.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids.

Preferred compounds of this invention are those in which $R_1$–$R_6$ are each hydrogen. Especially preferred are compounds which are enantiomerically pure stereoisomers of compounds where R is hydrogen and the indole ring is reduced or not reduced.

The compounds of this invention can be prepared according to the following scheme from commercially available starting materials or starting materials which can be prepared using literature procedures. Scheme 1 shows the preparation of a key intermediate and Scheme 2 shows the preparation of representative compounds of this invention.

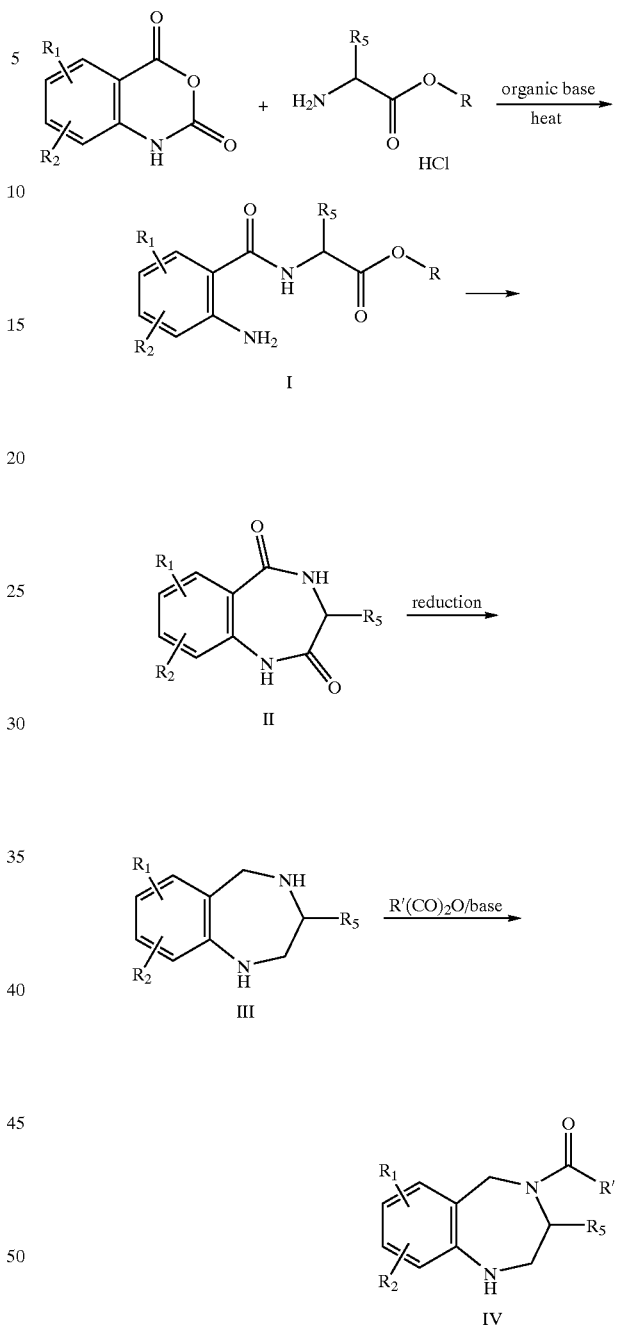

According to Scheme 1, a substituted or unsubstituted isatoic anhydride is allowed to react with substituted or unsubstituted glycine hydrochloride or an ester of the same in an organic base such as pyridine or triethylamine, to give either open-chain intermediate I or the benzodiazepinedione II. Intermediate I can be converted to intermediate II by heating in the presence of an acid, such as acetic acid. The benzodiazepinedione II is reduced to the benzodiazepine III using a reducing agent such as lithium aluminum hydride or a borane-tetrahydrofuran complex. The secondary nitrogen atom in III is protected using a protecting group, such as an amide by reacting III with an acylating agent, such as acetic anhydride, in the presence of a base, such as triethylamine, to give an acylated benzodiazepine IV.

Scheme 2

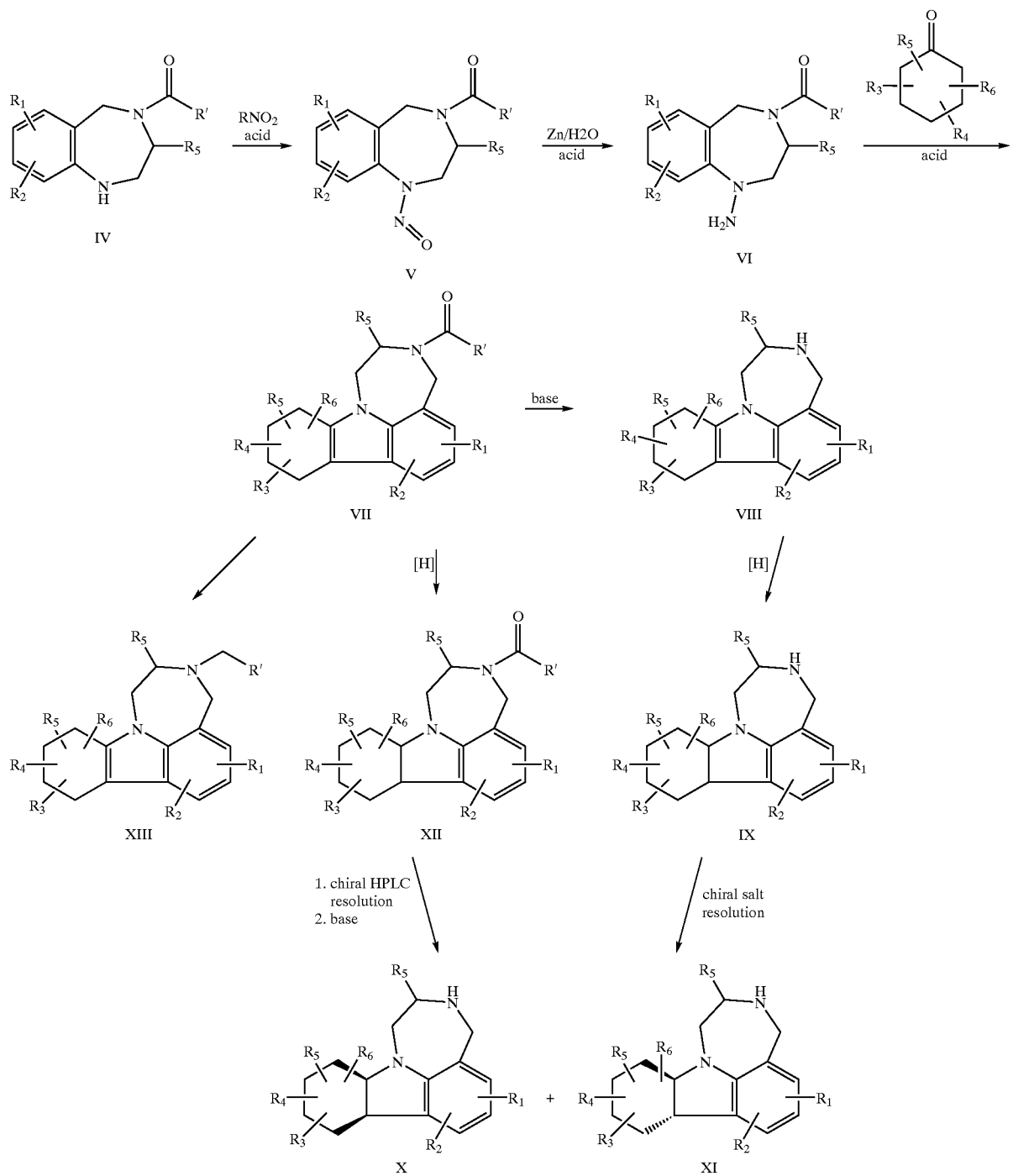

According to Scheme 2, Intermediate IV is allowed to react with a nitrosating agent, sodium nitrite, in the presence of an acid, such as acetic acid, to give nitroso compounds V. The nitroso compounds are reduced to hydrazines VI using a reducing agent, such as zinc powder in acetic acid and water. The hydrazines VI are allowed to react with substituted or unsubstituted cyclohexanones in acid, such as acetic acid, to give the fused indoles VII. The fused indoles VII can be treated with a base, such as NaOH, in a polar solvent, such as water or an alcohol, or with an acid, such as hydrochloric acid, to give the fused indoles VII, which are products of this invention. In addition, fused indoles VII can be reduced, such as by catalytic hydrogenation over a catalyst, such as palladium on charcoal, in an organic solvent, such as ethanol, in the presence of a trace of acid, such as trifluoroacetic acid, to give fused indolines IX which are products of this invention. Alternatively, fused indoles VII can be reduced, such as by catalytic hydrogenation over a catalyst, such as palladium on charcoal, in an organic solvent, such as ethanol, in the presence of a trace of an acid, such as trifluoroacetic acid, to give fused indolines XII. Fused indolines XII are diastereoisomeric mixtures which can be resolved using chiral HPLC to give separated diastereoisomers which can then be treated with an inorganic base, such as NaOH in a polar solvent, such as water or methanol at elevated temperatures, such as 50–100° C., to remove the acyl group giving diastereoisomers X and XI which are products of this invention. Enantiomers of X and XI can also be obtained by chiral salt resolution of racemic fused indolines X and XI using a resolving agent, such as benzoyltartaric acid, in an organic solvent, such as isopropyl alcohol. Finally, fused indoles VII can be reduced with a reducing agent, such as lithium aluminum hydride or a borane-THF complex to give XII which are compounds of this invention.

The acylation steps of this invention are understood to include reactions of the appropriate compound with any acylating agent and reaction conditions known in the art. Useful in these steps are acylating agents include acid halides and esters or anhyrides of the appropriate aliphatic carboxylic acid. Useful acid halides include acetyl chloride, propionyl chloride, isobutyryl chloride, benzoyl chloride, etc. Acid anhydrides include acetic anhydride and benzoic anhydride. Similarly, alkylation steps herein are understood to include any relevant alkylating agents and conditions known in the art. These include, but are not limited to the use of alkyl halides, such as methyl iodide, or alkyl tosylates or aldehyde alkylating agents in the presence of an applicable reducing agent.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known pharmaceutically acceptable acids. The processes herein will be understood to include an optional additional step of forming a salt form of the products via standard addition reactions with any pharmaceutically acceptable organic or inorganic acid.

The ability of the compounds of this invention to act as $5HT_{2C}$ agonists was demonstrated in several standard pharmacological test procedures, as described below.

Test Procedures
$5HT2_C$ Receptor Binding Test Procedure

To evaluate high affinity for the $5HT2_C$ receptor, a CHO (Chinese Hamster Ovary) cell line transfected with the CDNA expressing the human 5-hydroxytryptamine $2_C$ ($h5HT2_C$) receptor was maintained in DMEM (Dulbecco's Modified Eagle Media) supplied with fetal calf serum, glutamine, and the markers: guaninephosphoribosyl transferase (GTP) and hypoxanthinethymidine (HT). The cells were allowed to grow to confluence in large culture dishes with intermediate changes of media and splitting. Upon reaching confluence, the cells were harvested by scraping. The harvested cells were suspended in half volume of fresh physiological phosphate buffered saline (PBS) solution and centrifuged at low speed (900×g). This operation was repeated once more. The collected cells were then homogenized with a polytron at setting #7 for 15 sec in ten volumes of 50 mM Tris.HCl, pH 7.4 and 0.5 mM EDTA. The homogenate was centrifuged at 900×g for 15 min to remove nuclear particles and other cell debris. The pellet was discarded and the supernatant fluid recentrifuged at 40,000×g for 30 min. The resulting pellet was resuspended in a small volume of Tris.HCl buffer and the tissue protein content was determined in aliquots of 10–25 microliter ($\mu$l) volumes. Bovine Serum Albumin (BSA) was used as the standard in the protein determination by the method of Lowry et al., (J. Biol. Chem., 193:265 (1951). The volume of the suspended cell membranes was adjusted with 50 mM Tris.HCl buffer containing: 0.1% ascorbic acid, 10 mM pargyline and 4 mM $CaCl_2$ to give a tissue protein concentration of 1–2 mg per ml of suspension. The preparation membrane suspension (many times concentrated) was aliquoted in 1 ml volumes and stored at $-70°$ C. until used in subsequent binding experiments.

Binding measurements were performed in a 96 well microtiter plate format, in a total volume of 200 $\mu$l. To each well was added: 60 $\mu$l of incubation buffer made in 50 mM Tris.HCl buffer, pH 7.4 and containing 4 mM $CaCl_2$; 20 $\mu$l of [$^{125}$I] DOI (S.A., 2200 Ci/mmol, NEN Life Science).

The dissociation constant, KD of [$^{251}$I] DOI at the human serotonin $5HT_{2C}$ receptor was 0.4 nM by saturation binding with increasing concentrations of [$^{251}$I] DOI. The reaction was initiated by the final addition of 100.0 $\mu$l of tissue suspension containing 50 $\mu$g of receptor protein. Nonspecific binding is measured in the presence of 1 $\mu$M unlabeled DOI added in 20.0 $\mu$l volume. Test compounds were added in 20.0 ml. The mixture was incubated at room temperature for 60 min. The incubation was stopped by rapid filtration. The bound ligand-receptor complex was filtered off on a 96 well unifilter with a Packard® Filtermate 196 Harvester. The bound complex caught on the filter disk was dried in a vacuum oven heated to 60° C. and the radioactivity measured by liquid scintillation with 40 $\mu$l Microscint-20 scintillant in a Packard TopCount® equipped with six (6) photomultiplier detectors.

Specific binding is defined as the total radioactivity bound less the amount bound in the presence of 1 $\mu$M unlabeled DOI. Binding in the presence of varying concentrations of test drugs is expressed as percent of specific binding in the absence of drug. These results are then plotted as log % bound vs log concentration of test drug. Non linear regression analysis of data points yields both the IC50 and the Ki values of test compounds with 95% confidence limits. Alternatively, a linear regression line of decline of data points is plotted, from which the IC50 value can be read off the curve and the Ki value determined by solving the following equation:

$$Ki = \frac{IC50}{1 + L/KD}$$

where L is the concentration of the radioactive ligand used and the KD is the dissociation constant of the ligand for the receptor, both expressed in nM.

The following Ki's are provided for various reference compounds:

Ki value and 95% confidence interval.

| | |
|---|---|
| Ritanserin | 2.0 (1.3–3.1) nM |
| Ketanserin | 94.8 (70.7–127.0) nM |
| Mianserin | 2.7 (1.9–3.8) nM |
| Clozapine | 23.2 (16.0–34.0) nM |
| Methiothepin | 4.6 (4.0–6.0) nM |
| Methysergide | 6.3 (4.6–8.6) nM |
| Loxapine | 33.0 (24.0–47.0) nM |
| mCPP | 6.5 (4.8–9.0) nM |
| DOI | 6.2 (4.9–8.0) nM |

Stimulation of [$^3$H] Inositol Monophosphate production by $5HT_{2C}$ agonists.

CHO cells transfected with the cDNA expressing the human $5-HT_{2C}$ receptor were cultured in Dulbecco's modified Eagle's medium (DMEM) supplemented with 10% fetal bovine serum and non-essential amino acids. Upon reaching confluence the cells were harvested using PBS/EDTA and plated in 24 well plates at an initial density of $2.5 \times 10^5$ cells per well. One (1) ml of maintenance medium containing 1 $\mu$Ci/ml myo-[$^3$H] inositol was added to each well. After 48 hours labeling, the cells were washed once with 0.5 ml DMEM containing 25 mM HEPES and 10 mM LiCl, then preincubated with the medium for 30 min (antagonists were included in this period if tested). At the end of the preincubation, the medium was removed, the cells were then incubated with test compounds (in presence of antagonists if needed) for 30 min. The reaction was terminated by removal of the incubation solution and addition of 0.5 ml ice-cold 5% PCA, followed by 15 to 30 min incubation on ice. 200 $\mu$l of 0.5 M Tes/1.5 M $K_2CO_3$ was added to each well to neutralize to pH 7, and plates were left on ice for another 15 to 30 min to precipitate all salts. The liquid and solid phases were separated by centrifugation.

A portion (350 $\mu$l) of the upper aqueous phase was applied to Dowex AG-1X8 (formate form, 100–200 mesh) columns. The columns were then washed stepwise with 10 ml of water and 10 ml of 25 mM ammonium formate to remove free myo-[$^3$H]inositol and deacylated phosphoinositol, respectively. Finally 10 ml of 0.2 M ammonium formate solution was applied to the columns to elute [$^3$H] inositol monophosphate ([$^3$H] IP$_1$) directly into scintillation vials. Of this eluate, 1 ml was used to determine radioactivity by scintillation counting.

Agonist-stimulated levels of [$^3$H]inositol monophosphate (IP$_1$) is expressed as a percentage of the response observed with a maximally effective concentration of 5-HT (10 $\mu$M). A 3-parameter logistic function is used to generate estimate of $EC_{50}/IC_{50}$. Antagonists are tested in the presence of 10 $\mu$M 5-HT.

The following data are provided for various reference compounds:

| 5-HT | 15.1 nM | $EC_{50}$ |
| mCPP | 46.8 nM | $EC_{50}$ |
| | 60% | $E_{MAX}$ (relative to 5-HT) |
| SB200646 | 288 nM | $IC_{50}$ (10 $\mu$M 5-HT as agonist) |

Effects of Compounds on Feeding Behavior in Rats

Eight (8) male Sprague-Dawley rats weighing 150–180 g were separated into individual cages and acclimated to a powdered diet for 2 weeks. During this period and throughout the test procedure, the food cup and the animals were weighed daily. Following the acclimation period, animals were fasted for 24 hours and then injected with either vehicle or one of 4 doses of the test compound. Food intake was assessed at 2 and 24 hours following compound administration. Compounds to be evaluated were injected 1–2x per week until all animals had received all doses of the test compound. The order of doses were chosen using to a modified Latin Square design. Additional studies may be conducted in satieted rats at the start of the dark cycle. Compounds were injected i.p, s.c. or p.o. At the end of the study effects of the test compound on food intake was evaluated using a repeated measures ANOVA. Data were collected were 2 hour food intake (g). Data were subjected to one-way ANOVA with posthoc t-tests to assess group differences. Where appropriate, ED50 values were calculated. The ED50 value is the dose that produces a 50% reduction in food intake during the test period.

Results

Results from in vitro Test Procedures

| Compound | 5HT$_{2C}$ Affinity DOI/Agonist binding (Ki, nM) | 5HT$_{2C}$ % Emax (5HT, 100%) | Stimulation of IP3 (EC50, nM) |
|---|---|---|---|
| Example 1 | 56 | 90 | 426 |
| Example 2 | 92 | 70 | 207 |
| Example 3 | 73 | | |
| Example 4 | 243 | | |
| Example 5 | 358 | | |
| Example 6 | 599 | | |
| Example 7 | 452 | | |
| Example 8 | 189 | | |
| Example 9 | 55% inhibition @ 1 $\mu$M | | |

Results from in vivo 5HT$_{2C}$ Food Intake in Rats (24 hr fast)

| Compound | Route of Admin. | ED50 (mg/kg) |
|---|---|---|
| Example 1 | ip | 20.86 |

The results obtained in this standard pharmacological test procedures demonstrate that the compounds of this invention are 5HT$_{2C}$ receptor agonists useful for the treatment of diseases involving the central nervous system such as obsessive-compulsive disorder, depression, anxiety, generalized anxiety disorder, schizophrenia, panic disorder, migraine, sleep disorders, such as sleep apnea, eating disorders, such as hyperphagia, obesity, epilepsy, and spinal cord injury.

The compounds of this invention can be formulated neat or with one or more pharmaceutical carriers or excipients for administration, the proportion of which is determined by the solubility and chemical nature of the compound, chosen route of administration and standard pharmacological practice. The pharmaceutical carrier may be solid or liquid. This invention includes pharmaceutical compositions comprising a therapeutically or pharmaceutically effective amount of a compound described herein, or a pharmaceutically acceptable salt thereof, and a pharmaceutically acceptable carrier or excipient.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compounds of this invention can also be administered orally either in liquid or solid composition form.

The compounds of this invention may be administered rectally or vaginally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

As used herein, the terms "pharmaceutically effective amount" or "therapeutically effective amount" means the total amount of each active component of the pharmaceutical composition or method that is sufficient to show a meaningful patient benefit, i.e., treatment, prevention or amelioration of the cause or symptoms of the malady or condition, or an increase in rate of treatment, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of a compound of the present invention is administered to a mammal having a condition to be treated. Compounds of the present invention may be administered in accordance with the method of the invention either alone or in combination with other therapies such as treatments employing other pharmaceutical agents useful for treating or preventing the malady or condition in question or coexisting conditions or symptoms.

The dosage requirements vary with the particular compositions employed, the route of administration, the severity of the symptoms presented and the particular subject being treated. Based on the results obtained in the standard pharmacological test procedures, projected daily dosages of active compound would be 0.02 $\mu$g/kg–750 $\mu$g/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packaged powders, vials, ampoules, pre filled syringes or sachets containing liquids. The unit dosage form can be, for example, a capsule or tablet itself, or it can be the appropriate number of any such compositions in package form.

For human administration, daily dosages may be utilized from between about 0.5 $\mu$g/day to about 70,000 $\mu$g/day. More preferably, daily oral administration may include dosages from about 5 mg to about 500 mg, preferably from about 10 mg to about 200 mg, more preferably from about 10 mg to about 150 mg. Intravenous administration will be at a daily dose range of from about 0.5 mg to about 75 mg, preferably from about 1 mg to about 50 mg.

The following provides the preparation of compounds representative of this invention.

EXAMPLE 1

1,2,3,4,8,9,10,11-Octahydro-[4]diazepino[6,5,4-jk] carbazole (Based on the Procedure of D. H. Kim, U.S. Pat. No. 3,914,250)

Intermediate A. 4-Acetyl-2,3,4,5-tetrahydro-1H-benzodiazepine

Acetic anhydride (0.60 mL) was added dropwise to a stirred suspension of 2,3,4,5-tetrahydro-1H-benzodiazepine (950 mg, 6.4 mmol) in anhydrous ether (25 mL). After refluxing for four hours, the reaction mixture was filtered to remove a solid. Evaporation of the filtrate gave a residue which was purified by chromatography on silica gel eluting with 5% methanol in ethyl acetate. Evaporation of the product fractions gave an oil. The solid removed by filtration above contained a mixture of starting material and product by thin layer chromatography. The solid was partitioned between water and methylene chloride to remove salts and the organic portion was purified on silica gel as described above. Evaporation of the product fractions gave the product as an oil. Both product oils were dried under oil pump vacuum and gradually solidified. The first crop of intermediate A. (322 mg) melted at 83–85° C. (lit. mp: 84–86° C. recrystallized from ether). The second crop of intermediate A (450 mg) isolated from the solid, melted at 75–79° C.

Anal. Calcd. for $C_{11}H_{14}N_2O$; Theory: %C, 69.44; %H, 7.42; %N, 14.73; Found: %C, 69.6; %H, 7.52; %N, 14.71.

Intermediate B. 3-Acetyl-1,2,3,4,8,9,10,11-octahydro-[1,4]diazepino[6,7,1-jk]carbazole Intermediate A (450 mg, 2.36 mmol) was partially dissolved in water (3.8 mL) containing conc. HCl (0.23 mL)

while chilling in an ice/water bath. The ice bath was removed and a solution of NaNO$_2$ dissolved in water (0.4 mL) was added dropwise with stirring. A color change from yellow to yellow/brown resulted and an oil separated. The oil was extracted into methylene chloride, dried (MgSO$_4$), filtered and evaporated to give an oil which was dissolved in glacial acetic acid (5.4 mL). Powered zinc (1.16 g, 17.8 mmol, 7.5 eq) was added portionwise at 25–35° C. (exotherm) and the mixture was allowed to stir an additional hour after the addition of zinc was complete. The reaction mixture was filtered into a flask containing cyclohexanone (0.27 g, 2.6 mmol, 1.12 eq) and was heated at 100° C. for 1.5 h. The acetic acid was removed by evaporation under reduced pressure and the residue was purified by column chromatography on silica gel eluting with 5% methanol in methylene chloride to give 283 mg of a mixture which was further purified using chromatography on silica gel eluting with 7% methanol in ethyl acetate to give intermediate B as a yellow solid (65 mg, 10%) mp: 124–127° C. Lit. mp: 130–132° C. recrystallized from ether.

Anal. Calcd. For $C_{17}H_{20}N_2O$; Theory: %C, 76.08; %H, 7.51; %N, 10.44. Found: %C, 75.55; %H, 7.45; %N, 10.40.

Intermediate B was treated with conc. HCl and heated under reflux for 4 h. Within 2 h. a precipitate was observed. After chilling in an ice bath, the reaction mixture was filtered to give the HCl salt of the product of Example 1 as a white solid, mp: 314–317° C. (lit. mp: 318° C.)

Anal. Calcd. For $C_{15}H_{18}N_2$. HCl. 0.1 H$_2$O; Theory: %C, 68.07; %H, 7.31; %N, 10.59. Found: %C, 68.12; %H, 7.36; %N, 10.38.

EXAMPLE 2

1,2,3,4,7b,8,9,1 0,11,11a-Decahydro-[1,4]diazepino [6,7,1-jk]carbazole

The product of Example 1 (506 mg, 2.23 mmol) was dissolved in anhydrous THF and treated with 1M BH$_3$.THF (50 mL). The stirred reaction mixture was heated in an oil bath at 75–85° C. under a nitrogen atmosphere while trifluoroacetic acid was added gradually. After adding a total of 10 mL of trifluoroacetic acid and heating for 6 h, the reaction mixture was cooled to room temperature, treated with 6N HCl and stirred at room temperature overnight. The white solid which appeared was treated with conc. HCl (20 ml), warmed, swirled, and the volatiles were evaporated under reduced pressure. The white residue was suspended in methanol and evaporated two times to break up borane complexes. The residue was partitioned between ethyl acetate and aqueous NaOH. The organic phase was separated, dried (MgSO$_4$), and evaporated under reduced pressure to give a liquid residue which was purified by column chromatography on silica gel eluting with 10–20% methanol in methylene chloride. Evaporation of the pure fractions gave the product of Example 2 (80 mg) as an oil. The oil was dissolved in ether and treated with 1M HCl in ether to precipitate the dihydrochloride salt of the product of Example 2 (58 mg), mp: 265–269° C.

Anal. Calcd for $C_{15}H_{20}N_2$.2 HCl.1 H$_2$O; Calcd: %C, 56.43; %H, 7.58; %N, 8.77. Found: %C, 56.41; %H, 7.36; %N, 8.51.

EXAMPLE 3

8,8,10,10-Tetramethyl-1,2,3,4,8,9,10,11-octahydro[1,4] diazepino[6,7,1-jk]carbazole
Intermediate C. 4-Acetyl-2,3,4,5-tetrahydro-1H-benzodiazepin-1-ylamine To a chilled reaction vessel containing 3-acetyl-2,3,4,5-tetrahydro-1H-benzodiazepine (15.8 mmol) in H$_2$O (33 mL) and conc. HCl (1.8 mL) was added a solution of sodium nitrite (18.6 mmol) in H$_2$O (3.1 mL) dropwise. After the addition, the ice bath was removed and the reaction mixture was stirred at room temperature for 20 minutes. The reaction was diluted with H$_2$O and extracted two times with CHCl$_3$. The organic layers were washed with H$_2$O, dried (MgSO$_4$), filtered and concentrated under reduced pressure. The resulting oil was dissolved in AcOH (42 mL), chilled to 0° C., and zinc dust (138 mmol) added in small portions. The ice bath was removed and the reaction mixture was stirred at room temperature for 1.5 h. Celite was added to the reaction vessel and the reaction mixture was filtered through a pad of Celite. The filtrate was concentrated under reduced pressure to yield intermediate C.

$^1$H NMR (300 MHz, DMSO-d$_6$) δ 7.4–6.7(m, 6H), 4.4(m, 2H), 3.9–3.4(m, 2H), 3.1(m, 2H), 1.9(m, 3H).

Crude intermediate C (7.9 mmol) was dissolved in AcOH (50 mL) and a solution of 3,3,5,5-tetramethylcyclohexanone (9.5 mmol) in AcOH was added and heated under reflux for 18 h. The reaction mixture was cooled to room temperature, concentrated under reduced pressure to give an oil. The oil was purified by column chromato-graphy on silica gel eluting with EtOAc to yield 3-acetyl-8,8,10,10-tetramethyl-1,2,8,9,10, 11-octahydro-[1,4]diazepino[6,7,1-jk]carbazole as a light, brown foam/oil (1.0 mmol)

$^1$H NMR (300 MHz, DMSO-d$_6$) δ 7.48(m, 1H), 6.88(m, 2H), 4.87(m, 2H), 4.12(m, 2H), 3.96(m, 2H), 2.45(m, 1H), 2.00(m, 4H), 1.52(s, 2H), 1.33(s, 6H), 1.03(s, 6H).

3-Acetyl-8,8,10,10-tetramethyl-1,2,8,9,10,11-octahydro [1,4]diazepino[6,7,1-jk]-carbazole (1.0 mmol) was dissolved in conc. HCl (4.5 mL) and heated under reflux for 3 hours. The reaction was cooled to room temperature and the precipitate that formed was collected by filtration to give the hydrochloride salt of the compound of Example 3 as a tan solid (0.144 mmol).

Anal. Calc'd for $C_{19}H_{26}N_2$.HCl Theory. %C, 71.56; %H, 8.53; %N, 8.78. Found: %C, 71.61; %H, 8.74; %N, 8.62. $^1$H NMR (DMSO-d$_6$, 400 MHz) δ 9.75(s, 2H), 7.60(m, 1H), 6.99(m, 2H), 4.57(s, 2H), 4.29(m, 2H), 3.63(m, 2H), 2.48(m, 2H), 1.55(s, 2H), 1.37(s, 6H), 1.06(s, 6H). MS (+ESl, m/e(%)) 283(42, [M+H]$^+$).

EXAMPLE 4

9,9-Dimethyl-1,2,3,4,8,10,10,11-octahydro[1,4] diazepino[6,7,1-jk]carbazole

According to the procedure in Example 3, intermediate C (7.9 mmol) in glacial acetic acid (50 mL) was allowed to react with 4,4-dimethylcyclohexanone (9.48 mmol). The crude product was purified by chromatography on silica eluting with ethyl acetate to give 3-acetyl-9,9-dimethyl-1,2, 8,9,10,11-octahydro[1,4]diazepino[6,7,1 -jk]carbazole (2.4 mmol) as a tan foam/oil.

$^1$H NMR (300 MHz, DMSO-d$_6$) δ 7.23(m, 1 H), 6.90(m, 2H), 4.85(m, 2H), 4.2–3.9(m, 4H), 2.66(m, 2H), 2.39(s, 2H), 2.02(d, 3H), 1.60(m, 2H), 0.98(s, 6H).

The tan foam/oil (2.4 mmol) was treated with conc. HCl (10 mL) according to Example 3 to give the hydrochloride salt of the product of Example 4 (0.43 mmol) as a yellow solid.

Anal. Calc'd for $C_{17}H_{22}N_2$.HCl Theory: %C, 70.21; %H, 7.97; %N, 9.63. Found: %C, 70.39; %H, 8.07; %N, 9.60. $^1$H NMR (DMSO-d$_6$, 400 MHz) δ 9.73(s, 1H), 7.35(dd, J=1.5Hz, 1H), 6.98(m, 2H), 4.56(s, 2H), 4.27(m, 2H), 3.67

(m, 2H), 2.68(t, J=6.3 Hz, 2H), 2.42(s, 2H), 1.63(t, J=6.3 Hz, 2H), 0.99(s, 6H). MS (EI, m/e(%)) 254(100, M+), 226(22), 198(100).

EXAMPLE 5

6-Chloro-1,2,3,4,8,9,10,11-octahydro[1,4]diazepino [6,7,1-jk]cabazole

Intermediate D. 7-chloro-3,4-dihydro-1H-1,4-benzodiazepine-2,5-dione

5-Chloroisatoic anhydride (50.6 mmol) was stirred in $H_2O$ (95 mL) and $Et_3N$ (75.9 mmol) to give a homogenous solution. Glycine HCl (60.7 mmol) was added to the reaction mixture to give a milky solution. An additional 1.5 eq. of $Et_3N$ was added. The reaction mixture was stirred at room temperature for 18 hours. After the reaction mixture was concentrated under reduced pressure, acetic acid (170 mL) was added to the residue and the reaction mixture was heated under reflux for 72 hours. A precipitate formed upon cooling to room temperature. The solid was collected by filtration and washed with $H_2O$. The solid was dried under reduced pressure at 80° C. to give 20.9 mmol, 41% intermediate D.

$^1$H NMR (300 MHz, DMSO-$d_6$) δ 10.45(S, 1H), 8.67(m, 1H), 7.69(d, 1H), 7.57(dd, 1H), 7.12(d, 1H), 3.62(d, 2H).

THF (90 mL) was added to intermediate D to give a heterogenous solution. The reaction flask was cooled to 0° C. in an ice/$H_2O$ bath and 1M $BH_3$/THF solution (92 mL) was added via a dropping funnel. After the addition was complete, the reaction mixture was stirred at room temperature for 2 hours and heated under reflux for 18 h. The reaction mixture was cooled, methanol was added and the volatiles were removed under reduced pressure. This was repeated 3 times concentrated. The final residue was a yellow foam/oil. The crude material was crystallized in EtOAc to yield 12.5 mmol, 60% of 7-chloro-2,3,4,5-tetrahydro-1H-1,4-benzodiazepine.

$^1$H NMR (300 MHz, DMSO-$d_6$) δ 9.30(m, 1H), 7.34(m, 2H), 7.24(d,1H), 4.11,3.84(ABq, 2H), 3.58(m, 1H), 3.20(m, 2H), 2.91(m, 1H).

7-chloro-2,3,4,5-tetrahydro-1H-1,4-benzodiazepine (12.5 mmol) was dissolved in a mixture of THF (100 mL), $Et_3N$ (19.1 mmol) and acetic anhydride (12.4 mmol). The reaction mixture was heated under reflux for 18 h, cooled to room temperature and partitioned between $H_2O$ and EtOAc. The aqueous phase was extracted again 2× with EtOAc and the combined organic layers were dried over $MgSO_4$, filtered and concentrated to a yellow, oily solid. The crude material was purified by column chromatography on silia eluting with EtOAc to yield 3-acetyl-7-chloro-1,2,3,5-tetrahydro-4H-[1,4]benzodiazepine (2.8 mmol, 22%) as a clear oil.

$^1$H NMR (300 MHz, DMSO-$d_6$) δ 7.24(d, 1H), 7.03(m, 2H), 6.78(d, 1H), 5.80(m, 1H), 4.46(s, 1H), 4.38(s, 1H), 3.59(m, 2H), 3.09(m, 2H), 1.97(d, 3H).

To a chilled reaction vessel containing 3-acetyl-7-chloro-1,2,3,5-tetrahydro4H-[1,4]benzodiazepine (2.8 mmol) in $H_2O$ (5.3 mL) and concentrated HCl (321 μL) was added a solution of sodium nitrite (3.3 mmol) in $H_2O$ (535μL) dropwise. After the addition, the ice/$H_2O$ bath was removed and the reaction mixture was stirred at room temperature for 20 minutes. The reaction mixture was diluted with $H_2O$ (20 mL) and extracted 2× with $CHCl_3$. The combined organic layers were washed $H_2O$, dried ($MgSO_4$), filtered and concentrated under reduced pressure. The oily residue was dissolved in AcOH (7.5 mL), chilled to 0° C. in an ice/$H_2O$ bath, and zinc dust (24.5 mmol) was added in small portions. The ice bath was removed and the reaction mixture was stirred at room temperature for 1.5 hours. Celite was added and the reaction mixture was filtered through a pad of Celite into a round-bottom flask containing cyclohexanone (3.8 mmol). After heating under reflux for 3 h., the reaction mixture was cooled, concentrated under reduced pressure and the residue was purified by chromatography on silica gel eluting with ethyl acetate to give 3-acetyl-6-chloro-1,2,3,4, 8,9,10,11-octahydro[1,4]diazepino[6,7,1-jk]cabazole (0.770 mmol, 27%).

$^1$H NMR (300 MHz, DMSO-$d_6$) major rotamer δ 7.30(d, 1H), 7.03(d, 1H), 4.88(s, 2H), 4.18(m, 1H), 4.09(m, 1H), 4.01(m, 1H), 3.92(m, 1H), 2.67(m, 2H), 2.55(m, 2H), 2.01(s, 3H), 1.82(m, 2H), 1.71(m, 2H).

3-Acetyl-6-chloro-1,2,3,4,8,9,10,11-octahydro[1,4] diazepino[6,7,1-jk]cabazole (0.770 mmol ) was dissolved in conc. HCl (3.3 mL) and heated under reflux for 3.5 h. The reaction mixture was cooled to room temperature and the precipitate isolated by filtration, washed with a small amount of $H_2O$ and $Et_2O$ to yield the hydrochloride salt of the title compound (0.471 mmol, 61%) as a yellow solid.

Anal. Calc'd for $C_{17}H_{19}ClN_2$HCl: Theory: %C, 60.62; %H, 6.10; %N, 9.42. Found: %C, 60.62; %H, 6.15; %N, 9.29. $^1$H NMR (DMSO-$d_6$, 400 MHz) δ 9.95(s, 2H), 7.42(d, J=2.2Hz, 1H), 7.10(d, J=2.0 Hz, 1H), 4.56(s, 2H), 4.26(m, 2H), 3.62(m, 2H), 2.69(m, 2H), 2.59(m, 2H), 1.83(m, 2H), 1.73(m, 2H). IR (ATR, cm$^{-1}$) 2950, 2720, 2610, 2510, 2440, 2410,1580, 1460, 1440, 1390, 1330, 840. MS ((+)ESl, m/e(%)) 261(78, [M+H]+).

EXAMPLE 6

6-Methyl-1,2,3,4,8.9.10,11-octahydro[1,4]diazepino [6,7,1-jk]carbazole

Intermediate E: 4-Acetyl-7-methyl-2,3,4,5,tetrahydro-1H-benzodiazepine

6-Methylisatoic anhydride (10.0 g, 56 mmol) ethyl glycinate hydrochloride (9.77g, 1.25 equiv.) and anhydrous pyridine (200 mL) were combined and heated under reflux 3.5 h in a nitrogen atmosphere. The pyridine was removed by evaporation under reduced pressure to give an oil. The oil was dissolved in acetic acid (15 mL) and heated under reflux for 6 h. The volatiles were removed under reduced pressure to give a residue which was triturated methanol and filtered to recover 3.63 g of 6-methyl-3,4-dihydro-1H-1,4-benzodiazepine-2,5-dione as a yellow solid. The methanol filtrate was evaporated and acetic acid (200 mL) was added to the residue. The brown solution was heated under reflux overnight. The reaction mixture was cooled and the volume of acetic acid was reduced to half its volume under reduced pressure. Upon cooling, a solid precipitated which was collected. A second crop of 6-methyl-3,4-dihydro-1H-1,4-benzodiazepine-2,5-dione (4.7 g) was obtained as a beige solid.

6-Methyl-3,4-dihydro-1H-1,4-benzodiazepine-2,5-dione (9.3 g, 49 mmol) was suspended in anhydrous THF (150 mL) under a nitrogen atmosphere. To the suspension was added 1M $BH_3$ in THF (200 mL, 4 equiv.) and the reaction mixture was heated under reflux for 25 h. The reaction was quenched by the careful addition of 6N HCl (200 mL) with stirring under a nitrogen atmosphere. The acidic yellow solution was extracted with ethyl acetate 2 times. Additional water and saturated Nail solution were added to dissolve white solids. The layers were separated and the aqueous layer was chilled in an ice bath and adjusted to pH 14 with the addition of solid NaOH. The basic solution was extracted with ethyl acetate 3 times and the organic layers were combined, dried ($MgSO_4$), and evaporated under reduced pressure. The residue was dried under high vacuum to give 7-methylbenzodiazepine (5.76 g, 73%) as an oily solid mass.

According to the method of Intermediate A, Example 1, 7-methylbenzodiazepine (5.47 g, 34 mmol) was allowed to react with acetic anhydride (3.67 g, 34 mmol) in the presence of triethylamine (4 equiv.) in ether (500 mL) to give 7.29 g of Intermediate E as a yellow oil.

Intermediate E (7.29 g, 36 mmol) was dissolved in a mixture of water (560 mL) and conc. HCl (28 mL) and chilled in an ice bath. A solution of $NaNO_2$ (3.0 g, 43 mmol) in water (125 mL) was added from a dropping funnel over 30 minutes. The ice bath was left in place the reaction mixture was allowed to gradually warm to room temperature and stir overnight. The yellow solution was extracted with $CHCl_3$ 3 times. The organic layers were combined, dried and evaporated to give 5.28 g of crude nitroso compound. $[M+H-NO]^+$ @ m/z 204.

Intermediate F: 3-Acetyl-6-methyl-1,2,3,4,8,9,10,11-octahydro[1,4]diazepino-[6,7,1-jk]carbazole Zinc powder (3.27 g, 3 equiv.) was sonicated in water (10 mL) for 35 min. A solution of the nitroso compound (2.64 g, 11 mmol) dissolved in acetic acid (25 mL) was added rapidly dropwise with stirring to the cold reaction mixture. The ice bath was removed and stirring was continued for 1 hr. After the reaction mixture was filtered through a sintered glass funnel to remove zinc, the yellow filtrate was evaporated under reduced pressure (oil pump vacuum) to give a residue. The residue was dissolved in 1-propanol (60 mL) and p-toluenesulfonic acid hydrate (4.45 g) and cyclohexanone (6 mL, 3 equiv) were added. The reaction mixture was put into a pre-heated oil bath and heated under reflux for 1.5 h. The reaction mixture was cooled in an ice bath and neutralized (pH 6–7) with 2.5 N NaOH. The volatiles were evaporated under reduced pressure to give a solid plus oil. The residue was treated with acetonitrile and intermediate F was isolated as a crystalline solid: mp 180–183° C.

Intermediate F (340 mg, 1.2 mmol) was dissolved in conc. HCl (7 mL) and heated under reflux for 2 h. and then stirred at room temperature 2 h. The reaction mixture was chilled in an ice bath and filtered to collect 230 mg of the hydrochloride salt of the compound of Example 6.

Anal. Calcd. For $C16H20N2·HCl·0.25H_2O$ Theory: %C, 68.31; %H, 7.70; %N, 9.96. Found: %C, 68.70; %H, 7.67; %N, 9.94.

EXAMPLE 7

(2S)-2-Methyl-1,2,3,4,8,9,10,11-octahydro[1,4]diazepino[6,7,1-jk]carbazole

Following the method of Example 5 isatoic anhydride (61.3 mmol) was allowed to react with L-alanine ethyl ester HCl (73.6 mmol) in pyridine (200 mL) to give 29.7 mmol of (3S)-3-methyl-3,4-dihydro-1H-1,4-benzodiazepine-2,5-dione as a light, brown solid.

$^1$H NMR (300 MHz, DMSO-$d_6$) δ 10.33(s, 1H), 8.39(d, 1H), 7.72(dd, 1H), 7.48(m, 1H), 7.20(m, 1H), 7.08(d, 1H), 3.78(m, 1H), 1.21(d, 3H).

(3S)-3-methyl-3,4-dihydro-1H-1,4-benzodiazepine-2,5-dione (29.7 mmol) in THF (150 mL) and 1M $BH_3$/THF (130 mL) gave (3S)-3-methyl-2,3,4,5-tetrahydro-1H-1,4-benzodiazepine (24.6 mmol).

$^1$H NMR (300 MHz, DMSO-$d_6$) δ 9.00(s, 1H), 7.20(m, 4H), 3.94(d, 2H), 3.79(m, 1H), 3.53(m, 1H), 2.65(m, 1H), 1.07(d, 3H).

24.6 mmol of the above product was allowed to react with acetic anhydride (24.0 mmol) and $Et_3N$ (36.8 mmol) in DMF (50 mL) to give 1-[(3S)-3-methyl-1,2,3,5-tetrahydro-4H-1,4-benzodiazepin-4-yl]-1-ethanone (3.3 mmol) as a white solid after flash chromatography ($SiO_2$) using 90:10 EtOAc/hexane.

$^1$H NMR (300 MHz, DMSO-$d_6$) δ 7.15(m, 1H), 6.80(m, 1H), 6.52(s, 1H), 6.28(s, 2H), 4.22(m, 1H), 3.30(s, 3H, under $H_2O$ peak), 3.01 (m, 2H), 2.55(m, 2H), 1.22(m, 3H).

Reaction of 1-[(3S)-3-methyl-1,2,3,5-tetrahydro4H-1,4-benzodiazepin-4-yl]-1-ethanone (3.3 mmol) in $H_2O$ (6.4 mL) with $NaNO_2$ (3.9 mmol) and conc. HCl gave the nitroso compound which was allowed to reacted with ACOH (8.2 mL) and zinc dust (29.1 mmol) to afford the corresponding hydrazine. The hydrazine was allowed to react with cyclohexanone (4.5 mmol) in AcOH under reflux to give 1-[(2S)-2-methyl-1,2,8,9,10,11-hexahydro[1,4]diazepino[6,7,1-jk]carbazol-3(4M-yl]-1-ethanone (1.6 mmol) as a white solid.

$^1$H NMR (300 MHz, DMSO-d6) δ 7.21(dd, 1H), 6.85(m, 2H), 5.18(d, 1H), 4.90(m, 1H), 4.45(d, 1H), 4.24(dd, 1H), 4.11(dd, 1H), 2.66(m, 2H), 2.56(m, 2H), 1.89(s, 3H), 1.80 (m, 4H), 1.15(d, 3H).

The above compound (1.6 mmol) was heated under reflux with HCl (7.0 mL) to give the hydrochloride salt of the title compound 2S)-2-methyl-1,2,3,4,8,9,10,11-octahydro[1,4]diazepino[6,7,1-jk]carbazole, as white solid (0.690 mmol).

Anal. Calc'd for $C_{16}H_{20}N_2·HCl$: Theory: %C, 69.43; %H, 7.65; %N, 10.12. Found: %C, 69.27; %H, 7.61; % N, 9.88.

$^1$H NMR (DMSO-$d_6$, 400 MHz) δ 10.1 (br s,1H), 9.6(br s,1H), 7.36(dd, J=1.2 Hz, 1H), 6.99(m, 2H), 4.54(s, 2H), 4.39(dd, J=2.1 Hz, 1H), 3.97(m, 2H), 2.65(m, 4H) 1.76(m, 2H), 1.41(d, J=6.3 Hz, 3H).

IR (ATR, $cm^{-1}$) 2920, 2840, 2730, 2620, 2510, 2450, 1460, 1400, 1320, 740. MS (El, m/e(%)) 240(100, $M^+$), 198(100), 169(86),155(34).

EXAMPLE 8

(2R)-2-Methyl-1,2,3,4,8,9,10,11-octahydro[1,4]diazepino[6,7,1-jk]carbazole

Following the procedure of Example 5, D-alanine (73.6 mmol) and isatoic anhydride (61.3 mmol) were allowed to reflux in pyridine (50 mL) to give (3R)-3-methyl-3,4-dihydro-1H-1,4-benzodiazepine-2,5-dione (12.7 mmol) as a light brown solid.

$^1$H NMR (300 MHz, DMSO-$d_6$) δ 10.36(s, 1H), 8.40(d, 1H), 7.72(dd, 1H), 7.49(td, 1H), 7.20(td, 1H), 7.08(d, 1H), 3.80(m, 1H), 1.21(d, 3H).

(3R)-3-methyl-3,4-dihydro-1H-1,4-benzodiazepine-2,5-dione (12.7 mmol) was allowed to react with 60 mL 1M $BH_3$/THF to give (3R)-3-methyl-2,3,4,5-tetrahydro-1H-1,4-benzodiazepine as a white foam/clear oil (8.6 mmol).

$^1$H NMR (300 MHz, DMSO-$d_6$) δ 8.9(m, 1H), 7.24(m, 4H), 7.17(m, 1H), 3.94(d, 2H), 3.78(dd, 1H), 3.52(m, 1H), 2.65(m, 1H), 1.08(d, 3H).

(3R)-3-methyl-2,3,4,5-tetrahydro-1H-1,4-benzodiazepine (8.6 mmol) was allowed to react with 8.4 mmol acetic anhydride and 12.9 mmol $Et_3N$ in 20 mL DMF to give 2.9 mmol of 1-[(3R)-3-methyl-1,2,3,5-tetrahydro-4H-1,4-benzodiazepin4-yl]-1-ethanone.

$^1$H NMR (300 MHz, DMSO-$d_6$) major rotamer δ 6.90(m, 2H), 6.52(m, 2H), 5.69(m, 1H), 4.81, 4.18(Abq, 2H), 4.59 (m, 2H), 3.39(m, 1H), 3.05(m, 1H), 1.85(s, 3H), 0.98(d, 3H).

Using the same procedure as 1-[(2S)-2-methyl-1,2,8,9,10,11-hexahydro[1,4]diazepino[6,7,1-jk]carbazol-3(4M-yl]-1-ethanone with the previous compound (2.7 mmol), $NaNO_2$ (3.2 mmol), $H_2O$ (4 mL), HCl (308μL), AcOH (7 mL), zinc dust (23.6 mmol) and cyclohexanone (3.7 mmol) gave 0.531 mmol of 1-[(2R)-2-methyl-1,2,8,9,10,11-hexahydro[1,4]diazepino[6,7, 1-jk]carbazol-3(4H)-yl]-1-ethanone.

$^1$H NMR (300 MHz, DMSO-$d_6$) major rotamer δ 7.20(dd, 1H), 6.84(m, 2H), 5.18, 4.46(Abq, 2H), 4.90(m, 1H), 4.10 (m, 2H), 2.60(m, 4H), 1.89(s, 3H), 1.79(m, 4H), 1.15(d, 3H).

As described in Example 5, 1-[(2R)-2-methyl-1,2,8,9,10,11-hexahydro[1,4]diazepino[6,7,1-jk]carbazol-3(4H)-yl]-1-ethanone (0.531 mmol) gave the hydrochloride salt of the title compound (2R)-2-methyl-1,2,3,4,8,9,10,11-octahydro[1,4]diazepino[6,7,1-jk]carbazole as a light yellow solid (0.256 mmol).

Anal. Calc'd for C16H20N2.HCl.0.15H$_2$O: Theory: %C, 68.75; %H, 7.68; %N, 10.02. Found: %C, 68.36; %H, 7.66; %N, 9.81. $^1$H NMR (DMSO-d$_6$, 400 MHz) δ 10.06(br s, 1H), 7.36(d, J=7.6 Hz, 1H), 7.00(m, 2H), 4.56(s, 2H), 4.39(d, J=12.2 Hz, 1H), 3.95(m, 2H), 2.61(m, 4H), 1.80(m, 4H), 1.41(d, J=6.3 Hz, 3H). IR (ATR, cm$^{-1}$) 2920, 2845, 2710, 2630, 2510, 2450, 1460, 1400, 1330, 730. MS (El, m/e(%)) 240(88, M$^+$), 198(100), 99(76).

EXAMPLE 9

6-Chloro-3-ethyl-1,2,3,4,8,9,10,11-octahydro[1,4]diazepino[6,5,4-jk]carbazole

3-Acetyl-6-chloro-1,2,3,4,8,9,10,11-octahydro[1,4]diazepino[6,7,1-jk]cabazole was reduced with lithium aluminum hydride in THF by conventional methods to give an oil. The oil was dissolved in ether and treated with gaseous HCl to give the hydrochloride salt of the compound of Example 9, mp: 237–239° C.

What is claimed:

1. A compound of the formula:

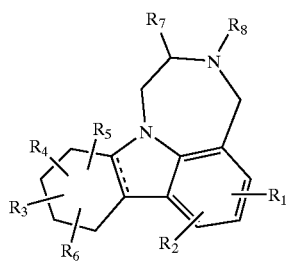

I wherein:
R$_1$ and R$_2$ are independently selected from hydrogen, alkyl of 1–6 carbon atoms, alkoxy of 1–6 carbon atoms, halogen, fluorinated alkyl of 1–6 carbon atoms, —CN, —NH—SO$_2$-alkyl of 1–6 carbon atoms, —SO$_2$—NH-alkyl of 1–6 carbon atoms, alkyl amide of 1–6 carbon atoms, amino, alkylamino of 1–6 carbon atoms, dialkylamino of 1–6 carbon atoms per alkyl moiety, fluorinated alkoxy of 1–6 carbon atoms, acyl of 2–7 carbon atoms, phenoyl or thiophenoyl;
R$_3$, R$_4$, R$_5$ and R$_6$ are independently selected from hydrogen, C$_1$–C$_6$ alkyl, C$_3$–C$_6$ cycloalkyl, C$_1$–C$_6$ alkoxy or C$_3$–C$_6$ cycloalkoxy;
R$_7$ is hydrogen or C$_1$–C$_6$ alkyl;
R$_8$ is hydrogen or C$_1$–C$_6$ alkyl; and
wherein the dashed line indicates an optional double bond;
or a pharmaceutically acceptable salt thereof; provided that when R$_1$ or R$_2$ is hydrogen, halogen or alkyl of 1 to 6 carbon atoms, at least one of R$_3$, R$_4$, R$_5$ or R$_6$ is not hydrogen.

2. A compound of claim 1 wherein R$_1$, R$_2$, R$_5$, R$_6$, R$_8$ and R$_7$ are each hydrogen and R$_3$ and R$_4$ are independently selected from hydrogen, C$_1$–C$_6$ alkyl, C$_3$–C$_6$ cycloalkyl, C$_1$–C$_6$ alkoxy or C$_3$–C$_6$ cycloalkoxy; or a pharmaceutically acceptable salt thereof.

3. A compound of claim 1 wherein R$_1$, R$_2$, R$_5$, R$_6$, R$_8$ and R$_7$ are each hydrogen and R$_3$ and R4 are independently selected from hydrogen, C$_1$–C$_6$ alkyl, C$_3$–C$_6$ cycloalkyl, C$_1$–C$_6$ alkoxy or C$_3$–C$_6$ cycloalkoxy, or a pharmaceutically acceptable salt thereof.

4. A compound of claim 1 which is 1,2,3,4,7b,8,9,10,11,11a-Decahydro-[1,4]diazepino[6,7,1jk]carbazole, or a pharmaceutically acceptable salt thereof.

5. A compound of claim 1 which is 8,8,10,10-Tetramethyl-1,2,3,4,8,9,10,11-octahydro[1,4]diazepino[6,7,1-jk]carbazole, or a pharmaceutically acceptable salt thereof.

6. A compound of claim 1 which is 9,9,Dimethyl-1,2,3,4,8,9,10,11-octahydro[1,4]diazepino[6,7,1-jk]carbazole, or a pharmaceutically acceptable salt thereof.

7. A compound of claim 1 which is 6-Methyl-1,2,3,4,8,9,10,11-octahydro[1,4]diazepino[6,7,1-jk]carbazole, or a pharmaceutically acceptable salt thereof.

8. A compound of claim 1 which is (2S)-2-Methyl-1,2,3,4,8,9,10,11-octahydro[1,4]diazepino[6,7,1-jk]carbazole, or a pharmaceutically acceptable salt thereof.

9. A compound of claim 1 which is (2R)-2-Methyl-1,2,3,4,8,9,10,11-octahydro[1,4]diazepino[6,7,1-jk]carbazole, or a pharmaceutically acceptable salt thereof.

10. A pharmaceutical composition comprising a pharmaceutically effective amount of a compound of claim 1, or a pharmaceutically acceptable salt thereof, and a pharmaceutically acceptable carrier or excipient.

11. A method of treatment of obsessive compulsive disorder in a mammal, the method comprising administering to a mammal in need thereof a pharmaceutically effective amount of a compound of the formula:

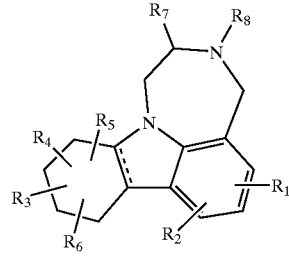

I wherein:
R$_1$ and R$_2$ are independently selected from hydrogen, alkyl of 1–6 carbon atoms, alkoxy of 1–6 carbon atoms, halogen, fluorinated alkyl of 1–6 carbon atoms, -CN, —NH—SO$_2$-alkyl of 1–6 carbon atoms, —SO$_2$—NH-alkyl of 1–6 carbon atoms, alkyl amide of 1–6 carbon atoms, amino, alkylamino of 1–6 carbon atoms, dialkylamino of 1–6 carbon atoms per alkyl moiety, fluorinated alkoxy of 1–6 carbon atoms, acyl of 2–7 carbon atoms, phenoyl or thiophenoyl;
R$_3$, R$_4$, R$_5$ and R$_6$ are independently selected from hydrogen, C$_1$–C$_6$ alkyl, C$_3$–C$_6$ cycloalkyl, C$_1$–C$_6$ alkoxy or C$_3$–C$_6$ cycloalkoxy;
R$_7$ is hydrogen or C$_1$–C$_6$ alkyl;
R$_8$ is hydrogen or C$_1$–C$_6$ alkyl; and
wherein the dashed line indicates an optional double bond;
or a pharmaceutically acceptable salt thereof.

12. The method of claim 11 wherein the mammal is a human.

13. A method of treatment of depression in a mammal, the method comprising administering to a mammal in need thereof a pharmaceutically effective amount of a compound of the formula:

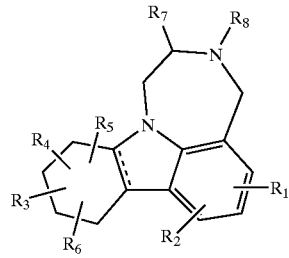

I wherein:
 R₁ and R₂ are independently selected from hydrogen, alkyl of 1–6 carbon atoms, alkoxy of 1–6 carbon atoms, halogen, fluorinated alkyl of 1–6 carbon atoms, —CN, —NH—SO₂-alkyl of 1–6 carbon atoms, —SO₂—NH-alkyl of 1–6 carbon atoms, alkyl amide of 1–6 carbon atoms, amino, alkylamino of 1–6 carbon atoms, dialkylamino of 1–6 carbon atoms per alkyl moiety, fluorinated alkoxy of 1–6 carbon atoms, acyl of 2–7 carbon atoms, phenoyl or thiophenoyl;
 R₃, R₄, R₅ and R₆ are independently selected from hydrogen, C₁–C₆ alkyl, C₃–C₆ cycloalkyl, C₁–C₆ alkoxy or C₃–C₆ cycloalkoxy;
 R₇ is hydrogen or C₁–C₆ alkyl;
 R₈ is hydrogen or C₁–C₆ alkyl; and
 wherein the dashed line indicates an optional double bond;
or a pharmaceutically acceptable salt thereof.

14. The method of claim 13 wherein the mammal is a human.

15. A method of treatment of anxiety in a mammal, the method comprising administering to a mammal in need thereof a pharmaceutically effective amount of a compound of the formula:

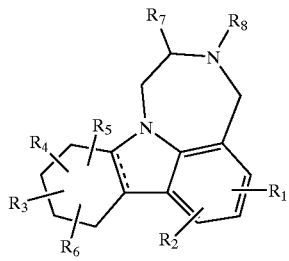

I wherein:
 R₁ and R₂ are independently selected from hydrogen, alkyl of 1–6 carbon atoms, alkoxy of 1–6 carbon atoms, halogen, fluorinated alkyl of 1–6 carbon atoms, —CN, —NH—SO₂-alkyl of 1–6 carbon atoms, —SO₂—NH-alkyl of 1–6 carbon atoms, alkyl amide of 1–6 carbon atoms, amino, alkylamino of 1–6 carbon atoms, dialkylamino of 1–6 carbon atoms per alkyl moiety, fluorinated alkoxy of 1–6 carbon atoms, acyl of 2–7 carbon atoms, phenoyl or thiophenoyl;
 R₃, R₄, R₅ and R₆ are independently selected from hydrogen, C₁–C₆ alkyl, C₃–C₆ cycloalkyl, C₁–C₆ alkoxy or C₃–C₆ cycloalkoxy;
 R₇ is hydrogen or C₁–C₆ alkyl;
 R₈ is hydrogen or C₁–C₆ alkyl; and
 wherein the dashed line indicates an optional double bond;
or a pharmaceutically acceptable salt thereof.

16. The method of claim 15 wherein the mammal is a human.

* * * * *